United States Patent [19]

Scholefield et al.

[11] Patent Number: 4,841,905
[45] Date of Patent: Jun. 27, 1989

[54] SAMPLE PROCESSING UNIT

[75] Inventors: John Scholefield, Kirkintilloch; Robert Johnston, Stewarton, both of Scotland

[73] Assignee: Automated Bacteria Counting Limited, Scotland

[21] Appl. No.: 115,061

[22] Filed: Oct. 1, 1987

[51] Int. Cl.⁴ ............................................. C23C 14/00
[52] U.S. Cl. ...................... 118/50; 118/404; 118/405; 427/434.7
[58] Field of Search ................ 118/50, 404, 405; 427/434.7

[56] References Cited

U.S. PATENT DOCUMENTS

| | | | |
|---|---|---|---|
| 3,964,434 | 6/1976 | Adler | 118/405 |
| 4,413,585 | 11/1983 | Weinhold et al. | 427/434.7 X |
| 4,643,126 | 2/1987 | Wilkinson et al. | 118/405 |

*Primary Examiner*—Stanley Silverman
*Attorney, Agent, or Firm*—Saidman, Sterne, Kessler & Goldstein

[57] ABSTRACT

A sample processing unit is disclosed for use in the a method of analysis, particularly autoanalysis, wherein the sample is presented for examination by deposition upon a tape substrate.

9 Claims, 3 Drawing Sheets

SAMPLE PROCESSING UNIT

This invention relates to a sample processing unit for use in a method of analysis, particularly an autoanalysis, wherein the sample is presented for examination by deposition upon a tape substrate.

Preparation of samples for study is often the most awkward and time-consuming step of any analysis. Frequently, preparation steps involve use of a number of different pieces of apparatus, messy reagents and accurate reproducibility of the sample preparation may be difficult leading to misleading results in analysis. In addition, the sample is often exposed to ambient influences during preparation so that further errors may arise from such open treatment of the sample.

Accordingly, it is an object of this invention to provide a compact unit for preparing a sample for examination, and thereby obviate or mitigate the aforesaid disadvantages.

According to this invention there is provided a sample processing unit comprising upper and lower body portions, said portions defining therebetween a through channel for receiving in use a sample carrier member and having formed therein at least one inlet port, at least one outlet port and associated inlet and outlet conduits connecting said ports with said channel, the arrangement being such that in use a sample borne upon a carrier member when positioned within the channel may be treated with an agent introduced through said inlet port(s) and excess agent may be removed through said outlet port(s) by application of a vacuum thereto.

Preferably, said channel is provided with a plurality of drainage channels grouped adjacent to the outlet conduit(s) of said unit, said drainage channels being disposed in a substantially transverse direction to the longitudinal length of the channel and venting through said outlet conduit(s) and outlet port(s).

Preferably, said drainage channels follow an arcuate path across said channel, the most preferred arrangement being that in which the radial centre of curvature of said drainage channels lies ahead of the intended path of a sample carrier member through the unit in use.

A preferred unit allows for multiple treatment steps, for example, staining, washing and drying, and provides a suitable number of inlet and outlet ports and drainage channels to fulfil the required function. In this case, to void cross interference between each treatment stage of the unit, it is preferred to provide a barrier, advantageously in the form of an air gap of sufficient breadth as to avoid capillary action, between each stage of the unit.

It is important to consider the intended use of the unit when selecting materials for its construction. When considering use of acidic reagents, an acrylic polymer has been found suitable, but stainless steel or any other corrosion-resistant material would suffice.

Embodiments of the invention will now be described, by way of example only, with reference to the accompanying drawings, in which.

Figure 1:
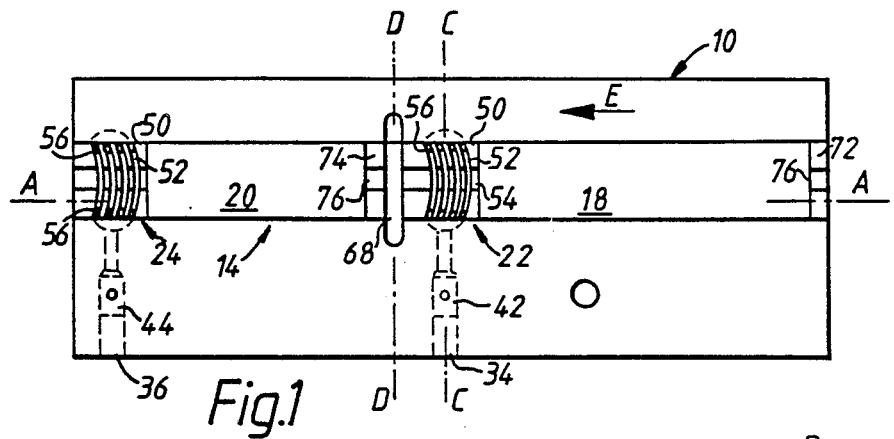
FIG. 1 is a plan view of the upper half of a processing unit embodying the invention.
Figure 2:
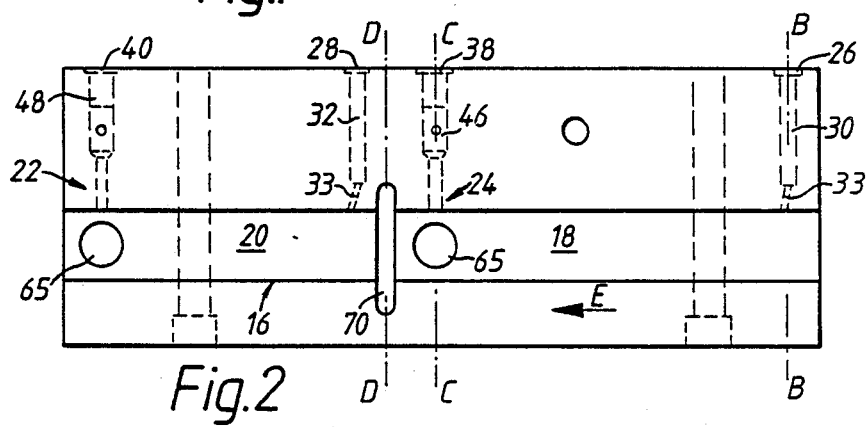
FIG. 2 is a plan view of the lower half of the same unit.
Figure 3:
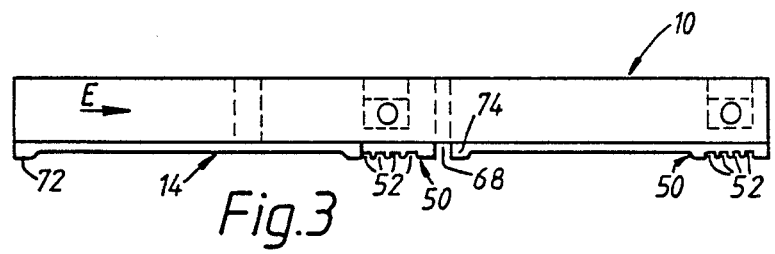
FIGS. 3 and 4 are side elevations of the unit of FIGS. 1 and 2.
Figure 4:
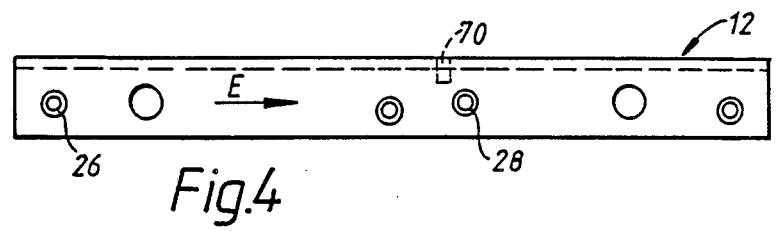
Figure 5:
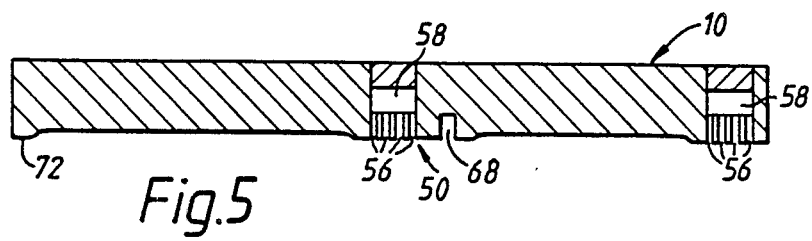
FIG. 5 is a section on line A—A of FIG. 1.
Figure 6:
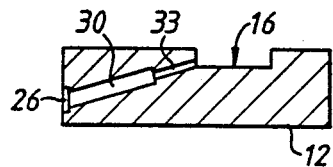
FIG. 6 is a section on line B—B of FIG. 2.
Figure 7:
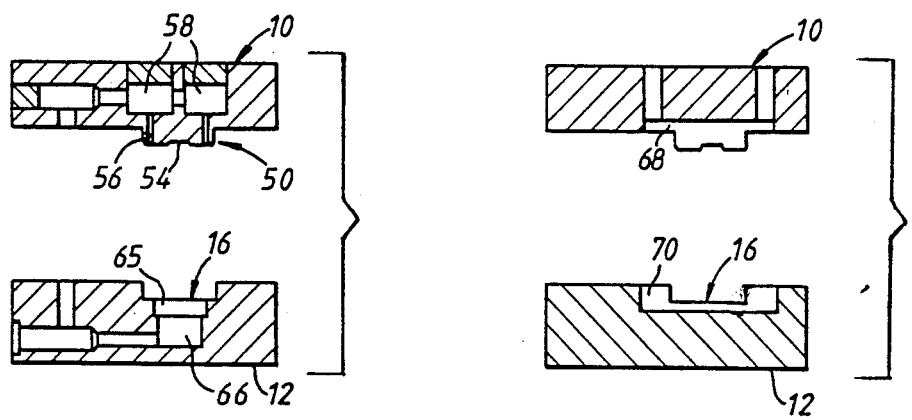
Figure 8:
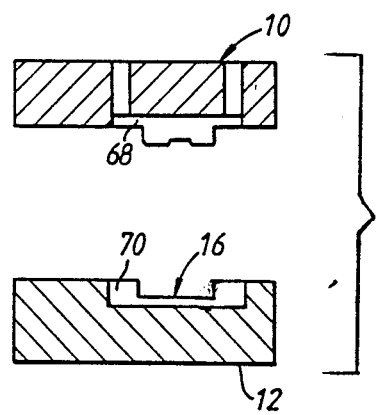
Figure 9:
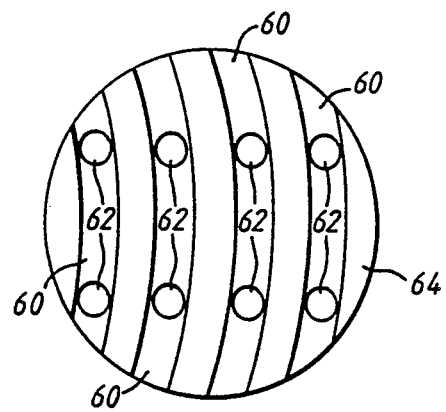
Figure 10:
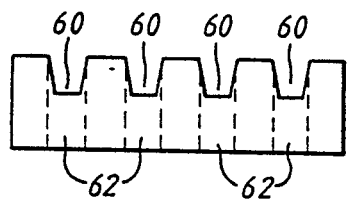
Figure 11:
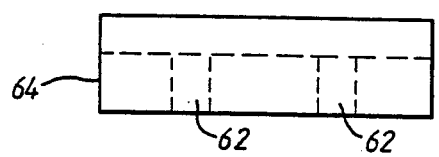

FIGS. 7 and 8 are sections on lines C—C and D—D respectively of FIGS. 1 and 2; and FIGS. 9, 10 and 11 are respectively a plan view and first and second elevations of a circular drainage insert for the lower half of FIG. 2.

Referring now to the drawings, a sample processing unit comprises a composite block consisting of an upper half 10 and a lower half 12. The upper half 10 is provided with an elongate longitudinal projection 14 extending along the length thereof and the lower half 12 with a cooperating longitudinal trough 16, so that, when assembled, a channel is defined through the composite block along which an elongate sample bearing medium, such as a tape substrate, may pass.

In the embodiment illustrated, the block provides a two-step processing unit, each of which steps includes a sample treatment stage 18 and 20 and a drying stage 22 and 24. In the present case, the first treatment stage 18 might be a staining process and second treatment stage 20, a washing process, the direction of tape travel being indicated by arrow E. The lower block-half 12 is provided with treatment fluid inlet ports 26 and 28 which communicate with the trough 16 via inlet channels 30 and 32. Thus, a staining solution might be applied to the tape via port 30 and wash water via port 32. The innermost portions 33 of the inlet channels 30 and 32 may be angled slightly forward in the direction of tape travel.

Following each of the treatment stages 18 and 20, the drying stages 22 and 24 serve to remove any excess treatment fluid from the sample and tape. For this purpose, both the upper and lower block-halves 10 and 12 are provided with outlet ports 34, 36, 38 and 40 which communicate with the tape channel via outlet channels 42, 44, 46 and 48 and drainage means described in more detail below. The outlet ports 34, 36, 38 and 40 are connected to a vacuum source (not shown).

In the case of the upper block-half 10, the drainage means for each of the drying stages 22 and 24 comprises a raised section 50 formed upon the elongate projection 14 which, in use, projects downwardly into the trough 16. The raised section has formed therein a series of parallel, arcuate transverse grooves 52 and a centrally disposed longitudinal groove 54. Drainage holes 56 are formed at either end of the arcuate grooves 52 adjacent the periphery of the longitudinal projection 14, and communicate with the outlet channels 42 and 44 via chambers 58 formed in the interior of the upper block-half 10.

The centres of curvature of the arcuate grooves 52 lie ahead of them in the direction of tape travel so that any fluid therein tends to be carried outwards towards the drainage holes 56 by the vacuum applied to the outlet ports 34, 36.

The drainage means of the lower back-half 12 are similar to those of the upper half 10, comprising a second series of arcuate grooves 60 with drainage holes 62 located in the floor of the trough 16. For ease of manufacture, these are preferably formed in circular inserts 64 (best seen in FIGS. 9, 10 and 11) which are inserted in corresponding openings 65 in the floor of the trough 16. In this case, the drainage holes 62 communicate with the outlet channels 46 and 48 via chambers 66 formed within the lower block-half 12.

In order to prevent any capillary leakage of treatment fluid between the first drying stage 22 and the second treatment stage 20, an air-break is formed in the tape channel by a pair of corresponding transverse grooves 68 and 70 in the upper and lower block-halves 10 and 12. Similar air-breaks (not shown) may also be formed along the lateral sides of the tape channel to prevent leakage from between the block-halves.

In order to ensure that the tape is maintained flat in the floor of the trough 16, further raised sections 72 and 74 having central longitudinal grooves 76 may be formed on the elongate projection 14 at the inlet end of the tape channel and following the air-break grooves 68 and 70.

Whilst the embodiment illustrated shows a two-step unit, the block may, of course, be formed as a single or multiple step processor depending upon the application.

The materials used may also depend upon the application, but acrylic, stainless steel, or other materials resistant to strong acid or bases are generally preferred.

We claim:

1. A sample processing unit comprising upper and lower body portions, said portions defining therebetween a through-channel for receiving in use a sample carrier member and having formed therein at least one inlet port, at least one outlet port and associated inlet and outlet conduits connecting said ports, the arrangement being such that in use a sample borne upon a carrier member when positioned within the channel may be treated with an agent introduced through the said inlet ports and excess agent may be removed through said outlet ports by application of a vacuum thereto to produce a dried sample, wherein the said through-channel is provided with a plurality of drainage channels, grouped adjacent to the outlet conduits and outlet ports of said unit, said drainage channels being disposed in a substantially transverse direction to the longitudinal length of the through-channel and venting through said outlet conduits and outlet ports.

2. A sample processing unit comprising upper and lower body portions, said portions defining therebetween a through-channel for receiving in use a sample carrier member and having formed therein at least one inlet port, at least one outlet port and associated inlet and outlet conduits connecting said ports, the arrangement being such that in use a sample borne upon a carrier member when positioned within the channel may be treated with an agent introduced through the said inlet ports and excess agent may be removed through said outlet ports by application of a vacuum thereto to produce a dried sample, wherein at least two treatment stages are defined therein, each of said stages having inlet and outlet ports and associated inlet and outlet conduits connecting said ports including drainage channels, each of said treatment stages being separated by an air-break defined in said through-channel by corresponding transverse grooves of sufficient width as to avoid capillary action causing cross-interferencee of agents used in each of said stages.

3. A sample processing unit comprising upper and lower body portions, said portions defining therebetween a through-channel for receiving in use a sample carrier member and having formed therein at least one inlet port, at least one outlet port and associated inlet and outlet conduits connecting said ports, the arrangement being such that in use a sample borne upon a carrier member when positioned within the channel may be treated with an agent introduced through the said inlet ports and excess agent may be removed through said outlet ports by application of a vacuum thereto to produce a dried sample, wherein said through-channel is adapted to receive a sample carrier member in the form of a flat tape and has raised sections formed therein for maintaining the tape in a flat condition within said through-channel.

4. A sample processing unit comprising upper and lower body portions, said portions defining therebetween a through-channel for receiving in use a sample carrier member and having formed therein at least one inlet port, at least one outlet port and associated inlet and outlet conduits connecting said ports, the arrangement being such that in use a sample borne upon a carrier member when positioned within the channel may be treated with an agent introduced through the said inlet ports and excess agent may be removed through said outlet ports by application of a vacuum thereto to produce a dried sample, wherein the inlet conduits have the innermost portion thereof angled forward in the direction of tape travel.

5. A sample processing unit comprising upper and lower body portions, said portions defining therebetween a through-channel for receiving in use a sample carrier member and having formed therein at least one inlet port, at least one outlet port and associated inlet and outlet conduits connecting said ports, the arrangement being such that in use a sample borne upon a carrier member when positioned within the channel may be treated with an agent introduced through the said inlet ports and excess agent may be removed through said outlet ports by application of a vacuum thereto to produce a dried sample, wherein the upper body portion is provided with an elongated longitudinal projection extending along the length thereof and the lower body portion with a corresponding longitudinal trough to define a channel through which there may be advanced a sample carrier member in the form of a tape, and inlet ports communicating with said trough via inlet channels are formed in the lower body portion, the innermost portions of said inlet channels being angled forwardly in the direction of tape travel through the channel, said lower body portion also having outlet ports communicating with the channel via outlet channels and lower drainage means provided therein, the upper body portion having corresponding upper drainage means venting through outlet channels to outlet ports the said upper drainage means in the upper body portion comprising a raised section formed upon the elongate projection which, in use, projects downwardly into the trough, which section has formed therein a series of parallel, arcuate transverse grooves and a centrally disposed longitudinal groove, each of said grooves having drainage holes adjacent the periphery of the longitudinal projection which communicate with the outlet channels via chambers formed in the interior of the upper body portion, and the said lower drainage means comprising a second series of parallel arcuate grooves with drainage holes communicating with the outlet channels via chambers formed within the lower body portion.

6. A sample processing unit according to claim 1 wherein the said drainage channels follow an arcuate path across said through-channel and drainage holes are formed at either end of the said drainage channels.

7. A sample processing unit according to claim 6 wherein the radial centre of curvature of said drainage channels lies ahead of the intended path of a sample carrier member through the unit in use.

8. A sample processing unit according to claim 6 or claim 7 wherein the drainage channels are defined by cooperating raised and recessed sections located in the through-channel at least one of which connections is formed from a removable insert which is locatable in an opening defined in the floor of said through-channel.

9. A sample processing unit according to claim 5 wherein at least one air-break is formed in the through-channel by providing corresponding transverse grooves in the upper and lower body portions and wherein additional raised sections having central longitudinal grooves are formed on the elongate projection at least at one end of the through-channel and adjacent to the air-break(s) defined by the transverse grooves.

* * * * *

UNITED STATES PATENT AND TRADEMARK OFFICE
CERTIFICATE OF CORRECTION

PATENT NO. : 4,841,905

DATED : June 27, 1989

INVENTOR(S) : John Scholefield et al.

It is certified that error appears in the above—identified patent and that said Letters Patent is hereby corrected as shown below:

Title page  under the heading "U.S. PATENT DOCUMENTS" insert

-- 3,675,400   7/1972   Viktora et al...........
   3,845,703   12/1974  Gibbs et al.............
   4,071,315   1/1978   Chateau ................ --

Title page , below the section "U.S. PATENT DOCUMENTS" insert

--              FOREIGN PATENT DOCUMENTS 0 148 290   12/1983  European Patent Office
   2.178.711   9/1973   France
   85/05691    12/1985  Patent Cooperation Treaty
   25 37 095   2/1977   West Germany --

In the Specification:

Column 1, line 48, delete "void" and insert --avoid--;

Column 6, line 4, delete "(s)".

Signed and Sealed this

Twenty-second Day of May, 1990

*Attest:*

HARRY F. MANBECK, JR.

*Attesting Officer*          *Commissioner of Patents and Trademarks*